United States Patent [19]

Tiep et al.

[11] Patent Number: 4,535,767

[45] Date of Patent: Aug. 20, 1985

[54] OXYGEN DELIVERY APPARATUS

[76] Inventors: Brian L. Tiep, 632 Norumbega Dr., Monrovia, Calif. 91016; Robert E. Phillips, 12217 Iredell St., Studio City, Calif. 91601; Ben A. Otsap, 7661 Airport Blvd., Los Angeles, Calif. 90045

[21] Appl. No.: 432,187

[22] Filed: Oct. 1, 1982

[51] Int. Cl.³ ............................................. A61M 16/00
[52] U.S. Cl. ............................ 128/207.18; 128/205.17; 128/207.16
[58] Field of Search ...................... 128/207.18, 207.16, 128/205.13, 205.14, 203.22, 204.24, 204.26, 205.17, 205.15, 205.16, 205.25, 205.12, 202.29

[56] References Cited

U.S. PATENT DOCUMENTS

| | | | |
|---|---|---|---|
| 2,535,938 | 12/1950 | Lombard | 128/205.17 |
| 2,677,371 | 2/1954 | Serra | 128/205.17 |
| 3,794,021 | 2/1974 | Lambertsen | 128/205.17 |
| 3,973,564 | 8/1976 | Carden | 128/204.28 |
| 4,054,133 | 10/1977 | Myers | 128/207.18 |
| 4,106,505 | 8/1978 | Salter et al. | 128/207.18 |
| 4,120,300 | 10/1978 | Tiep | 128/204.24 |
| 4,256,101 | 3/1981 | Ellestad | 128/204.23 |

FOREIGN PATENT DOCUMENTS

| | | | |
|---|---|---|---|
| 1136544 | 12/1956 | France | 128/205.17 |
| 934973 | 8/1963 | United Kingdom | 128/205.17 |

Primary Examiner—Henry J. Recla
Assistant Examiner—Karin M. Reichle
Attorney, Agent, or Firm—Edward D. O'Brian; K. H. Boswell

[57] ABSTRACT

An apparatus for delivering oxygen to a patient is preferably constructed so as to include an elongted, deformable receptacle having an open side extending along its length, a flexible, "floppy" diaphragm secured at its edge so as to seal off or enclose the open side of the receptacle and a retainer for protecting and for limiting expansion of the diaphragm located along the side of the diaphragm remote from the receptacle. As the apparatus is used, oxygen is constantly delivered to the extremities of the receptacle through appropriate supply lines. On exhalation exhaled gas is forced by the pressure of the breath through a cannula—preferably a nasal cannula—into the interior of the receptacle remote from the supply lines. This cannula is used so that gas can flow. This exhaled gas is used to force the diaphragm against the retainer, opening up the interior of the receptacle in an amount such that some of the exhaled gas will be held in the receptacle. This latter gas will gradually be replaced by the oxygen. On inhalation this mixture will be drawn through the cannula into the body as a consequence of the partial vacuum created during inhalation. This will have the effect of collapsing the diaphragm against the interior of the receptacle so as to substantially close off the interior of the receptacle between the cannula and the supply lines.

7 Claims, 7 Drawing Figures

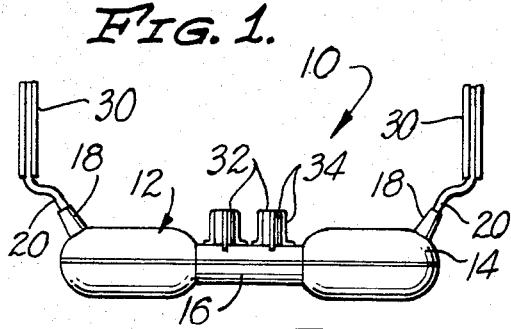
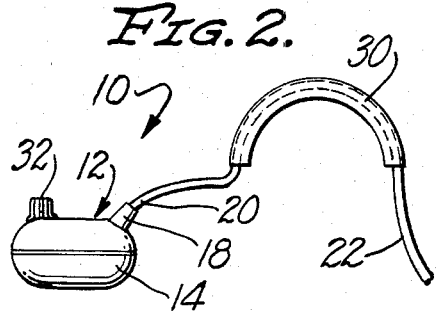
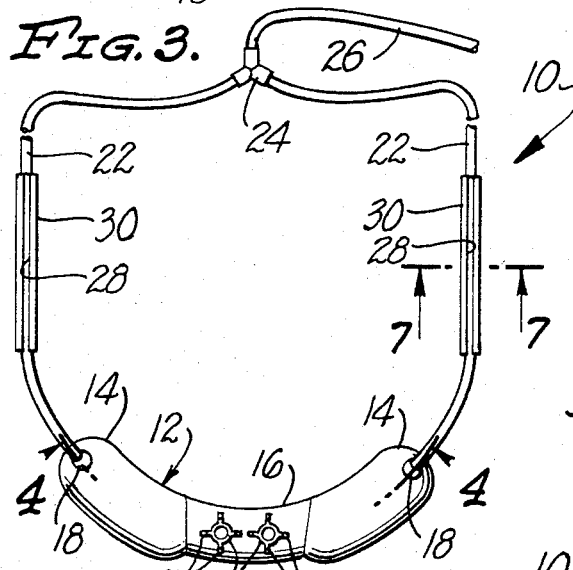
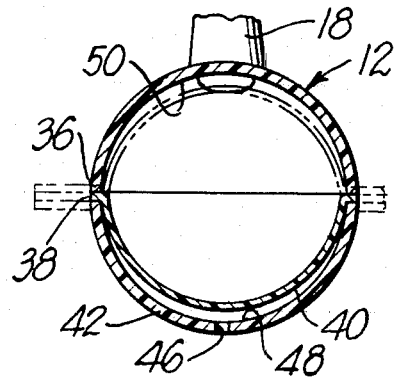
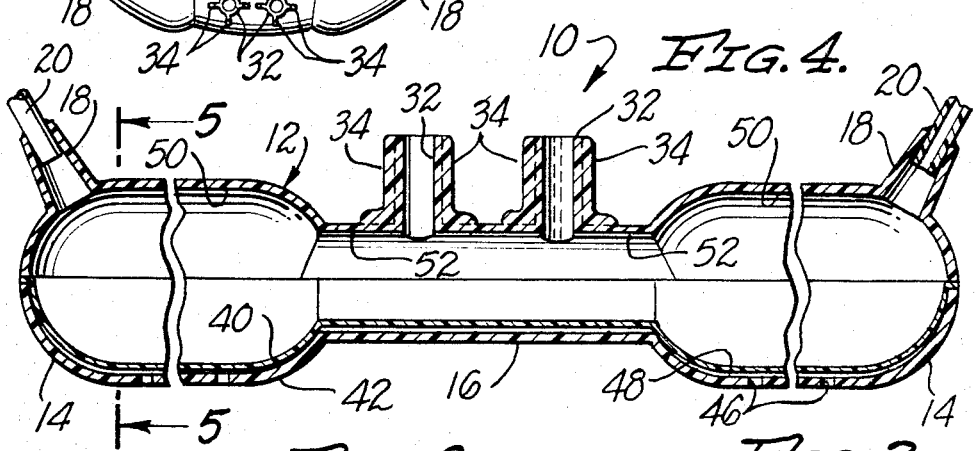
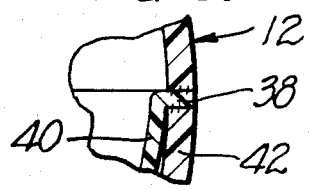
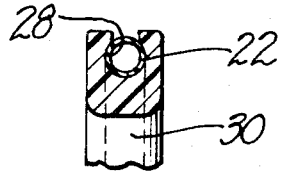

OXYGEN DELIVERY APPARATUS

BACKGROUND OF THE INVENTION

The invention set forth in the specification pertains to a new and improved oxygen delivery apparatus. It also pertains to a new and improved method of delivering oxygen which is practiced utilizing this apparatus.

Virtually everyone is aware of the fact that it is frequently necessary or advisable to deliver oxygen enriched air or other gases or gas mixtures to patients during various different types of therapy. It is not considered that an understanding of the present invention requires an understanding of or a detailed discussion of all of the various different types of apparatus which have previously been developed for the purpose of administering oxygen or oxygen enriched gaseous mixtures in connection with various different types of therapy. It is, however, considered important to note that it is generally believed that none of the various different apparatuses developed for administering oxygen is as acceptable as normally desired for any one of a variety of different reasons.

Amongst these reasons are various items concerning factors such as cost and reliability. Another particularly important factor in connection with the acceptability of prior oxygen delivery apparatus concerns whether or not such apparatus results in the use of a minimal amount of oxygen reasonably approaching only the amount of oxygen actually required or needed in connection with the treatment of a patient. This is particularly important because of the relatively high cost of oxygen of a purity normally required in connection with the treatment of a human body.

SUMMARY OF THE INVENTION

It is believed that it will be apparent from the preceding that there is a need for new and improved apparatus for delivering oxygen to a patient. There is also considered to be a related need for a new and improved method of delivering oxygen to a patient which overcomes certain of the limitations of prior methods for delivering oxygen to a patient. Broadly, the present invention is intended to provide both a new and improved apparatus and a new and improved method which are intended to fulfill these closely related needs.

More specifically, the present invention is intended to provide an apparatus which can be easily and conveniently constructed at a comparatively nominal cost, which is very simple to utilize and which will operate in an intended manner over a very prolonged period with substantially no maintenance. The invention is also intended to provide a method as indicated in the preceding which can be easily and conveniently practiced. Both the apparatus and process objectives of the present invention are also directed to the delivery of oxygen to a patient in such a manner as to minimize the amount of oxygen used and, hence, so as to minimize the cost to the patient of the oxygen used. This latter and the simple, effective character of the apparatus of the present invention are considered to be quite important.

In accordance with this invention, those various objectives indicated in the preceding pertaining to an apparatus are achieved by providing an oxygen delivery apparatus including cannula means for use in conveying gases into and out of the human body, oxygen supply line means for conveying oxygen to said apparatus and inhalation and exhalation responsive flow control means connected to said cannula means and said supply line means for controlling the flow of oxygen to said cannula means as said apparatus is used in which the improvement comprises: said flow control means including an elongated diaphragm means defining an enclosed chamber extending between said cannula means and supply line means, said cannula means and said supply line means being spaced from one another by said diaphragm a sufficient distance so that gas flow from said supply line means will be capable of substantially displacing any gas from within said chamber by forcing gas from within said chamber out through said cannula means, said diaphragm means being formed of a flexible material which is capable of changing in configuration in response to pressures as are developed during inhalation and exhalation and being capable of expanding so as to receive gas during exhalation and being capable of being moved in response to inhalation so as to substantially close off the interior of said chamber generally between said supply line means and said cannula means.

In accordance with this invention, those various objectives indicated in the preceding pertaining to a method or process are achieved by providing a process for delivering oxygen to the human body through the use of inhalation and exhalation responsive flow control means, oxygen supply line means for conveying oxygen to said flow control means and cannula means for use in conveying gases into and out of the human body to and from said flow control means in which the improvement comprises: constantly supplying oxygen to the interior of said flow control means, utilizing the initial inhalation during breathing so as to supply the lungs with an oxygen from within the interior of said flow control means, substantially closing off the interior of said flow control means so that there is no flow from said supply line means to said cannula means as soon as a quantity of gas from within said flow control means has been inhaled, then finishing the inhalation part of the breathing cycle by inhaling ambient air and next using the initial part of the breath on the exhalation to open up the interior of said flow control means and to fill said flow control means with exhaled gas as soon as the receiptacle is filled, venting the remainder of the exhaled gas to the ambient atmosphere and then displacing exhaled gas from the interior of said flow control means with oxygen supplied to the interior of said flow control means.

BRIEF DESCRIPTION OF THE DRAWING

Because of the nature of this invention, it is best more fully explained with reference to the accompanying drawing in which:

FIG. 1 is a top plan view of a presently preferred apparatus in accordance with this invention;

FIG. 2 is a side elevational view of the apparatus as it appears in claim 1;

FIG. 3 is a view of the apparatus shown in FIG. 1 in which various parts are shown in elevation after two tubes, illustrated in FIG. 1 have been bent so that the parts appear as they are shown in this figure;

FIG. 4 is a partial cross-sectional view taken at the curved line 4—4 in FIG. 3;

FIG. 5 is a partial cross sectional view taken at line 5—5 of FIG. 4;

FIG. 6 is an enlarged fragmentary view of a part of FIG. 5; and

FIG. 7 is an enlarged cross-sectional view taken at line 7—7 of FIG. 3.

The specific apparatus illustrated in the drawing is constructed so as to utilize the principles or concepts of the present invention verbally expressed in the appended claims. Those skilled in the field of the design and construction of various different types of apparatus for administering oxygen to a patient will realize that these concepts and principles can be employed in a variety of somewhat differently appearing apparatuses through the use or exercise of routine engineering skill in their field on the basis of the disclosure embodied within this specification. For this reason, this invention is to be considered as being limited solely by the appended claims.

DETAILED DESCRIPTION

In the drawing there is shown an apparatus 10 of the present invention which is constructed so as to include an elongated, imperforate receptacle 12 more or less having a shape of an inverted trough. This receptacle 12 is preferably formed out of a reasonably self supporting, pliable, somewhat resilient, somewhat flexible material such as rubber or rubber like material so that it may be distorted from its normal configuration to fit adjacent to the face of a patient and so that it will not be uncomfortable to the patient when in contact with a patient's skin. It may, however, be formed of other materials. This receptacle 12 is shaped so as to include somewhat bulbous extremities 14 connected by an elongated, necked down section 16. This section 16 preferably is slightly longer than the distance across the base of the nostrils of an individual (not shown).

Small tubular nipples 18 are provided on the extremities 14 remote from the center section 16. These nipples 18 are adapted to contain the ends 20 of small tubes 22 used for the purpose of conveying oxygen to the remainder of the apparatus 10. Preferably, these tubes 22 are joined by a common Y fitting 24 to a common line 26 going to a pressure regulator (not shown) and supply tank for delivering oxygen (not shown). The individual tubes 22 are preferably of such a size that they can be easily snapped or popped into grooves 28 in small holders 30 shaped so as to fit behind the ears of a patient in the manner of which the bows of glasses fit behind a patient's ears.

The receptacle 12 is also provided with integrally formed tubes or cannula 32 which are shaped and spaced from one another in such a manner as to be capable of being fitted within the nostrils of a patient (not shown) without causing the patient any significant or material discomfort. These cannula 32 are located so as to extend off of the section 16 generally midway between the two nipples 18. These cannula 32 must be sufficiently small in diameter so that they will not effectively close off or block the nostrils of a patient. Thus, the cannula 32 are of such a dimension that when they are used air will flow around the exterior of these cannula 32.

In order to avoid any possibility of the cannula 32 fitting inside the nostrils so as to block air flow around them it is possible to form them so that they include small radially projecting fins 34 which will serve to space them more or less in the center areas of nostrils. When such fins 34 are used it is also considered preferable to extend them to a limited extent along the section 16 as shown in FIGS. 1 and 4 so as to avoid any possibility of the section 16 fitting against the face of the user in such a manner as to effectively block or impede air flow generally around or passed it as the apparatus 10 is used in the intended manner. When the receptacle 12 is formed of a pliable rubber or rubber like material as indicated in the preceeding, these fins 34 will normally be small enough in dimension as to be capable of adequate flexure so as to minimize any discomfort to a patient.

The receptacle 12 has an open side (not separately numbered) defined by a side edge 36. This edge 36 supports and is secured to a flange like edge 38 of an elongated diaphragm 40 by any convenient means such as, for example, vulcanization. This diaphragm 40 is preferably formed of a flexible material such as rubber or a rubber like composition which is capable of changing in configuration as hereinafter indicated during the use of the apparatus 10 in response to pressures as are developed by a patient during inhalation and during exhalation and as are apparent at the cannula 32. This diaphragm 40 is essentially of a loose, "floppy", pliable character and is capable of being moved between positions as are discussed in this specification as the apparatus 10 is used.

This diaphragm 40 is covered by a retainer 42 manufactured out of a rubber or rubber-like material such as is used in manufacturing the receptacle 12 having an edge 44 which overlies the edge 38 and which is attached to it by any convenient method such as, for example, through vulcanization to the edge 38 and to the edge 36. This retainer 42 can also be formed of a much harder material inasmuch as this retainer 42 does not normally come in contact with a patient as the apparatus 10 is used. When the retainer 42 is formed of such a harder material, it may be curved or bowed slightly so as to serve to hold the receptacle 12 in a configuration closely conforming to the shape of a face with the cannula 32 in place in the nostrils. It is to be noted that the edges 36, 38 and 44 need not be sealed together but can be secured together in any convenient manner such as for example through the use of conventional flange connections (not shown).

In the apparatus 10 the retainer 42 is used for the purpose of protecting the diaphragm 40 and for the purpose of limiting the amount that the diaphragm 40 can expand outwardly generally away from the receptacle 12. In order for the retainer 42 to effectively serve this latter purpose, it is provided with a plurality of different vent openings 46 which prevent air from being trapped between the diaphragm 40 and this retainer 42. Preferably the interior 48 of the retainer 42 is substantially a mirror image of the interior of the receptacle 12 so as to avoid the the diaphragm 40 having to be capable of stretching in order to be capable of being supported by either the interior 48 or the interior 50 as the apparatus 10 is used. As a consequence of this, it is possible to use materials in forming the diaphragm 40 which are not "stretchy" in character but are of such a nature as to be capable of being forced or of being pushed to either of two locations—against the interior 48 or against the interior 50—as a result of the pressure of the breath as the apparatus 10 is used.

The use of this apparatus 10 is quite simple. To be used it must be located upon the face of a patient with the cannula 32 in the patient's nostrils and preferably with the holders 30 supporting the remainder of the device by being positioned over the ears of the patient. Either before or after the apparatus is located in this manner oxygen will be supplied to the line 26 in a comparatively low volume at a pressure as subsequently indicated. As soon as both the oxygen is supplied as noted and the apparatus 10 is in place, the patient should commence breathing in a normal manner.

As the patient starts to exhale if the diaphragm 40 is against the retainer 42 the gas within the receptacle 12 and the oxygen being supplied to this receptacle 12 will normally exert a sufficient back pressure so that exhaled gas will flow between the nostrils of the patient and the cannula 32 to the ambient. Then as the patient starts inhaling the gas from the volume within the receptacle 12 enclosed by the diaphragm 40 will be drawn in through the cannula 32 and into the lungs of the patient. During the initial inhalation gas will be drawn from within the interior of the receptacle 12 because of the positions of the cannula 32 generally within the center region of the nostrils of a patient normally there will be some limited gas flow from the ambient around the exterior of the cannula 32. Such resistance is a result of the normal considerations relative to fluid control. Nevertheless, there will be some minor amounts of flow around the cannula 32 until the gas within the receptacle 12 becomes exhausted.

As this occurs, the diaphragm 40 will change its orientation from against the interior 48 to against the interior 50. Normally, this change in orientation will not result in any gas being trapped within the interior of the receptacle 12. In case a problem should be encountered with such entrapment because of a particular design of an apparatus 10 it is considered preferable to use small flow channels 52 in the section 16 leading to the extremities 14 which will not be blocked or filled by the diaphragm 40 as it moves in this manner.

At the point that the gas mixture within the receptacle 12 is exhausted ambient air is drawn in to the body of an individual through the space around the cannula 32 until at the end of the inhalation cycle expiration starts. Then, preferentially, the initial exhaled gas will flow through the cannula 32 for substantially the same reasons that there was preferential flow through the cannula 32 on inhalation. There will be some minor amount of exhaled gases that will be vented around the cannula 32 during the initial part of this exhalation. As the initial exhalation occurs, the diaphragm 40 will "flop" up against the surface 48 and the receptacle 12 will become filled. After this occurs because of the build up of pressure within the receptacle 12, the remaining exhaled gas will be vented directly to the ambient around the cannula 32. At the end of the exhalation cycle the inhalation cycle as described in the preceding will be resumed.

During these cycles oxygen will be continuously entering the receptacle 12. The quantity or bolus of expired gas used to fill the receptacle 12 on exhalation will consist of expired gas which only reached the upper part of the respiratory tract of an individual and which, as a result of this will not contain the same quantity of gases normally given off by the body through the lungs as the gas which is exhaled during the last part of an exhalation cycle. The quantity or bolus of gas inhaled using the apparatus at the start of the inhalation cycle from the receptacle 12 will be the first gas to enter the lungs on inhalation and, hence, will be the gas which is most important in connection with oxygen therapy.

These factors are important in connection with another matter—the pressure of the oxygen supplied to the receptacle 12 through the tube 22. Normally, the oxygen flowing through the tubes 22 will be at a pressure which is high enough to displace any expired air trapped within the receptacle 12 and will be at a volume which is such that at least 50% of the exhaled gas caught within the receptacle 12 will be purged or displaced from within the interior of the receptacle 12 prior to the start of an inhalation cycle. Preferredly the pressure and volume of oxygen used are such that an amount of oxygen is supplied corresponding to about from 80 to about 120% of the volume of the expired gas trapped within the receptacle 12. Any oxygen supplied in excess of the amount necessary to displace substantially all the expired gas from within the receptacle 12 will move through the cannula 32 and will be entrained within expired gas moving to the ambient. Any oxygen moved in this manner will be moved toward the end of the exhalation cycle and at least some of it will normally be in a position relative to the nose of a person such that some of this oxygen will tend to be inhaled at the start of the inhalation cycle.

At the start of an inhalation cycle the volume of gas inhaled from within the receptacle 12 as well as a partial vacuum caused by the inhalation will tend to move the diaphragm 40 against the interior 50. Such movement can be roughly compared to the movement of a metastable diaphragm such as a common bowed oil can bottom from one of its two positions to the other. This will have the effect of retarding oxygen flow from the lines 22 through the receptacle 12 for a brief time interval. During this time period the oxygen flow through the lines 22 will, to a degree, move and open up the diaphragm 40 to a sufficient extent so that some oxygen will be retained by the diaphragm 40 within the receptacle 12 in areas remote from the cannula 32. If, for any reason, the inhalation cycle is undesirably long or if the oxygen pressure is higher than is indicated, the only effect of this will be that the diaphragm 40 will be displaced to a sufficient extent so as to permit some limited direct flow through the receptacle 12 to the cannula 32 from the lines 22.

On the start of an exhalation cycle the pressure of the exhaled gas will be sufficient so as to completely move the diaphragm 40 as previously described more or less in the manner in which a metastable diaphragm goes from one of its positions to another. Of course, at this point the sequence of operations described will recommence.

By making the internal capacity of the receptacle 12 comparatively limited it is possible to utilize this sequence of operations as described in the preceeding in order to supply an amount of oxygen such as is normally required in connection with most forms of oxygen therapy while concurrently holding down the amount of oxygen used to an extent that it is quite significant from a financial standpoint. It is presently considered that satisfactory oxygen therapy along with concurrent minimization of oxygen usage are achieved when the volume within the receptacle 12 which can be contained within this receptacle and the diaphragm is from about 3 to about 20% of the tidal volume of an anticipated user of the apparatus 10. Preferred results are achieved when this range is from about 5 to about 10%. On occasion it is possible to obtain satisfactory results with a few patients when the volume of the receptacle 12 is less than this amount. This is particularly the case when the amount of oxygen required during therapy is limited. The use of a receptacle having a larger volume is considered to be primarily detrimental because when such a larger volume is used, the user cannot effectively exhaust the entire contents of the volume. As a consequence of this, a desired degree of oxygen concentration is not normally achieved when a larger volume is used.

It is to be noted that the apparatus 10 need not be utilized only in the manner described in the preceeding. On occasion a patient may not have normal use of his or her nasal passages. In these circumstances the cannula 32 can be held in the mouth of the individual in such a manner that air flow around the cannula is not restricted to any significant extent. If it is desired to provide an apparatus corresponding to the apparatus 10 which is only suitable for use by individuals having impaired nasal passages a single cannula 32 can be substituted for the two cannula 32 illustrated. It is considered that whenever reasonably possible the use of an apparatus in accordance with this invention in the mouth of the patient should be avoided so as to keep the mouth of the patient free.

We claim:

1. An oxygen delivery apparatus including cannula means for use in conveying gases into and out of the human body through the nostrils, oxygen supply line means for conveying oxygen to said apparatus and inhalation and exhalation responsive flow control means connected to said cannula means and said supply line means for controlling the flow of oxygen to said cannula means as said apparatus is used in which the improvement comprises:

said cannula means being sufficiently small so that they will not close off air flow through the nostrils of the human body, said flow control means including an elongated receptacle with first and second opposite ends and defining an open sided elongated chamber extending therebetween, said supply line means connected into the interior of said chamber and said cannula means connected to the interior of the chamber, said receptacle further having an elongated diaphragm means formed of flexible material and mounted on said receptacle over said open side thereby enclosing said chamber, said diaphragm means being mounted transversely to said cannula means to move forward and away from said cannula means, said supply line means and said cannula means spaced from one another by said chamber a sufficient distance so that gas flow from said supply line means will be through said enclosed chamber and will be capable by forcing gas from within said chamber out through said cannula means, said supply line means being connected to said cannula only through the interior of said chamber, said diaphragm means having a side opposite the side adjacent said enclosed chamber communicating with the surrounding atmosphere, said diaphragm means being sufficiently flexible and responsive to pressures that are developed during inhalation and exhalation so as to receive gas in said chamber during exhalation and to substantially close off the flow of gas between said supply line means and cannula means through said chamber in response to inhalation.

2. An apparatus as claimed in claim 1 wherein:

said receptacle is an elongated, impermeable self-supporting receptacle, said supply line means includes two separate tubes each of which is connected to said receptacle, one of said tubes being in communication with the interior of one end of said receptacle, the other of said tubes being in communication with the interior of the other end of said receptacle, said cannula means includes two nasal cannula located on said receptacle intermediate the ends of said receptacle, said nasal cannula means being sufficiently small so that they will not close off air flow through the nostrils of the human body, said flow control means also including retainer means attached to said receptacle and located along the side of said diaphragm communicating with the atmosphere, said retainer means being capable of limiting the movement of said diaphragm generally away from said receptacle on exhalation so that the total volume enclosed within said chamber on exhalation corresponds to the volume of oxygen enriched gas to be delivered to the lungs of the patient at the start of inhalation.

3. An apparatus as claimed in claim 2 wherein:

said receptacle is formed of a pliable, flexible material so as to avoid discomfort to the human body as a result of contact between said receptacle and the skin of the body as said apparatus is used, said nasal cannula are integral with said receptacle, said diaphragm, said receptacle and said retainer means have edges which are secured together so as to enclose said chamber and the volume between said diaphragm and the interior of said retainer means.

4. An apparatus as claimed in claim 3 wherein:

fin means on said nasal cannula means for avoiding any possibility of said nasal cannula means fitting within the nostrils of the human body so as to block air flow around them.

5. An apparatus as claimed in claim 4 wherein:

said receptacle has bulbous extremities at said first and second opposite ends and an elongated necked down center section extending between said extremities, said tubes being connected to the ends of said extremities, respectively, remote from one another, said cannula being located on said necked down section.

6. An apparatus as claimed in claim 1 wherein:

said receptacle is an elongated, impermeable self supporting receptacle, said supply lines means includes two separate tubes, each of which is connected to said receptacle, one of said tubes being in communication with the interior of one end of said receptacle, the other of said tubes being in communication with the interior of the other end of said receptacle, said cannula means includes two nasal cannula located on said receptacle intermediate the ends of said receptacle, said cannula means being sufficiently small so that they will not close off air flow through the nostrils of the human body, said receptacle is formed of a pliable, flexible material so as to avoid discomfort to the human body as a result of contact between said receptacle and the skin of the body as said apparatus is used, said nasal cannula are integral with said receptacle, said flow control means also including retainer means attached to said receptacle and located along the side of said diaphragm communicating with the atmosphere, said retainer means being capable of limiting the movement of said diaphragm generally away form said receptacle on exhalation so that the total volume enclosed within said chamber on exhalation corresponds to the volume of oxygen enriched gas to be delivered to the lungs of the patient at the start of inhalation, said diaphragm, said receptacle and said retainer means have edges which are secured together so as to enclose said chamber and the volume between said diaphragm and the interior of said retainer means, fin means on said nasal cannula means for avoiding any possibility of said nasal cannula means fitting within the nostrils of the human body so as to block air flow around them, said receptacle has bulbous extremities at said first and second opposite ends and an elongated necked down center section extending between said extremities, said tubes being connected to the ends of said extremities, respectively, remote from one another, said cannula being located on said necked down section, the capacity of said chamber when inflated is from about 3 to about 20% of the tidal volume of the breath of the anticipated user of said apparatus.

7. An apparatus as claimed in claim 6 wherein:

the capacity of said chamber when inflated is from about 5 to about 10% of the tidal volume of the breath of the anticipated user of the apparatus.

* * * * *

UNITED STATES PATENT AND TRADEMARK OFFICE
CERTIFICATE OF CORRECTION

PATENT NO. : 4,535,767
DATED : AUGUST 20, 1985
INVENTOR(S) : TIEP, et al

It is certified that error appears in the above-identified patent and that said Letters Patent are hereby corrected as shown below:

```
Column 2, line 58, "claim 1" should be --Fig. 1--.
Column 4, line 2, "passed" should be --past--.
Column 4, line 53, delete one of the words "the".
Column 9, line 4, "form" should be --from--.
```

Signed and Sealed this

Twenty-eighth Day of January 1986

[SEAL]

Attest:

DONALD J. QUIGG

Attesting Officer

Commissioner of Patents and Trademarks